United States Patent
Kang et al.

(10) Patent No.: US 11,864,871 B2
(45) Date of Patent: Jan. 9, 2024

(54) WEARABLE DEVICE AND METHOD OF MEASURING BIO-SIGNAL

(71) Applicant: SAMSUNG ELECTRONICS CO., LTD., Suwon-si (KR)

(72) Inventors: Jae Min Kang, Seoul (KR); Seung Woo Noh, Seongnam-si (KR); Sang Yun Park, Hwaseong-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 88 days.

(21) Appl. No.: 17/091,832

(22) Filed: Nov. 6, 2020

(65) Prior Publication Data

US 2021/0386298 A1    Dec. 16, 2021

(30) Foreign Application Priority Data

Jun. 15, 2020  (KR) .................. 10-2020-0072335

(51) Int. Cl.
| | |
|---|---|
| *A61B 5/024* | (2006.01) |
| *A61B 5/0205* | (2006.01) |
| *A61B 5/00* | (2006.01) |
| *A61B 5/02* | (2006.01) |
| *A61B 5/16* | (2006.01) |

(52) U.S. Cl.
CPC .......... *A61B 5/0205* (2013.01); *A61B 5/0002* (2013.01); *A61B 5/0077* (2013.01); *A61B 5/02007* (2013.01); *A61B 5/02416* (2013.01); *A61B 5/165* (2013.01); *A61B 5/681* (2013.01); *A61B 5/6803* (2013.01); *A61B 2560/0214* (2013.01)

(58) Field of Classification Search
None
See application file for complete search history.

(56) References Cited

U.S. PATENT DOCUMENTS

| | | | |
|---|---|---|---|
| 8,647,270 | B2 | 2/2014 | LeBoeuf et al. |
| 8,700,111 | B2 | 4/2014 | LeBoeuf et al. |
| 8,788,002 | B2 | 7/2014 | Leboeuf et al. |
| 8,886,269 | B2 | 11/2014 | LeBoeuf et al. |

(Continued)

FOREIGN PATENT DOCUMENTS

| | | |
|---|---|---|
| CN | 105877729 A | 8/2016 |
| JP | 2011-251007 A | 12/2011 |

(Continued)

OTHER PUBLICATIONS

A.H. Titus et al. (2011). CMOS Photodetectors. 10.5772/20194. <https://www.researchgate.net/publication/221914021_CMOS_Photodetectors>.viewed on Jun. 1, 2022 (Year: 2011) :unselected:.*

(Continued)

*Primary Examiner* — Lynsey C Eiseman
*Assistant Examiner* — James Moss
(74) *Attorney, Agent, or Firm* — Sughrue Mion, PLLC

(57) ABSTRACT

A wearable device includes an external light collector configured to collect external light; a sensor including an auxiliary light source and a light receiver, and configured to measure a bio-signal of an object; and a processor configured to determine whether the external light is sufficient to measure the bio-signal, and to control driving of the auxiliary light source based on the determination.

24 Claims, 16 Drawing Sheets

(56) References Cited

U.S. PATENT DOCUMENTS

| | | | |
|---|---|---|---|
| 8,923,941 B2 | 12/2014 | LeBoeuf et al. | |
| 8,929,965 B2 | 1/2015 | LeBoeuf et al. | |
| 8,929,966 B2 | 1/2015 | LeBoeuf et al. | |
| 8,934,952 B2 | 1/2015 | LeBoeuf et al. | |
| 8,942,776 B2 | 1/2015 | LeBoeuf et al. | |
| 8,961,415 B2 | 2/2015 | LeBoeuf et al. | |
| 8,989,830 B2 | 3/2015 | LeBoeuf et al. | |
| 9,131,312 B2 | 9/2015 | LeBoeuf et al. | |
| 9,289,135 B2 | 3/2016 | LeBoeuf et al. | |
| 9,289,175 B2 | 3/2016 | LeBoeuf et al. | |
| 9,301,696 B2 | 4/2016 | LeBoeuf et al. | |
| 9,314,167 B2 | 4/2016 | LeBoeuf et al. | |
| 9,750,462 B2 | 9/2017 | LeBoeuf et al. | |
| 9,955,919 B2 | 5/2018 | LeBoeuf et al. | |
| 9,986,324 B2 | 5/2018 | Pergament et al. | |
| 10,076,282 B2 | 9/2018 | LeBoeuf et al. | |
| 10,092,245 B2 | 10/2018 | LeBoeuf et al. | |
| 10,334,348 B2 | 6/2019 | Pergament et al. | |
| 10,448,840 B2 | 10/2019 | LeBoeuf et al. | |
| 10,542,593 B1 | 1/2020 | Mignoli et al. | |
| 10,613,032 B2 | 4/2020 | Ahn et al. | |
| 10,716,480 B2 | 7/2020 | LeBoeuf et al. | |
| 10,735,848 B2 | 8/2020 | Pergament et al. | |
| 10,750,954 B2 | 8/2020 | LeBoeuf et al. | |
| 2009/0274347 A1* | 11/2009 | Gat | A61B 5/073 |
| | | | 382/128 |
| 2010/0217100 A1 | 8/2010 | LeBoeuf et al. | |
| 2011/0245637 A1* | 10/2011 | McKenna | G01J 3/10 |
| | | | 356/319 |
| 2014/0135596 A1 | 5/2014 | LeBoeuf et al. | |
| 2015/0126824 A1 | 5/2015 | LeBoeuf et al. | |
| 2015/0148636 A1* | 5/2015 | Benaron | A61B 5/02405 |
| | | | 600/328 |
| 2015/0342467 A1 | 12/2015 | LeBoeuf et al. | |
| 2016/0324432 A1* | 11/2016 | Ahmed | A61B 5/0255 |
| 2016/0367196 A1 | 12/2016 | Kim et al. | |
| 2017/0079534 A1 | 3/2017 | Tchertkov et al. | |
| 2017/0172430 A1 | 6/2017 | Zhao et al. | |
| 2017/0188851 A1 | 7/2017 | LeBoeuf et al. | |
| 2018/0078151 A1* | 3/2018 | Allec | A61B 5/1455 |
| 2018/0192950 A1 | 7/2018 | LeBoeuf et al. | |
| 2018/0228435 A1 | 8/2018 | LeBoeuf et al. | |
| 2018/0296166 A1 | 10/2018 | LeBoeuf et al. | |
| 2019/0000396 A1 | 1/2019 | LeBoeuf et al. | |
| 2019/0008460 A1 | 1/2019 | LeBeouf et al. | |
| 2019/0082974 A1 | 3/2019 | LeBoeuf et al. | |
| 2019/0099130 A1 | 4/2019 | LeBoeuf et al. | |
| 2019/0129470 A1 | 5/2019 | Hasei et al. | |
| 2019/0357780 A1 | 11/2019 | Ko et al. | |

FOREIGN PATENT DOCUMENTS

| | | |
|---|---|---|
| JP | 2017-159052 A | 9/2017 |
| JP | 2019-082876 A | 5/2019 |
| KR | 10-0660349 B1 | 12/2006 |
| KR | 10-2013-0067505 A | 6/2013 |
| KR | 10-2016-0149015 A | 12/2016 |
| KR | 10-2017-0088343 A | 8/2017 |
| KR | 10-2018-0078206 A | 7/2018 |
| KR | 10-1948605 B1 | 2/2019 |
| KR | 10-2019-0058176 A | 5/2019 |
| KR | 10-2019-0081527 A | 7/2019 |
| KR | 10-2019-0134319 A | 12/2019 |
| WO | 2013/042070 A1 | 3/2013 |

OTHER PUBLICATIONS

Jim Lucas, What is Visible Light, https://www.livescience.com/50678-visible-light.html, May 23, 2022, viewed on Jan. 23, 2023.*
Communication dated Jun. 23, 2021 by the European Patent Office in counterpart European Patent Application No. 20217824.0.

* cited by examiner

WEARABLE DEVICE AND METHOD OF MEASURING BIO-SIGNAL

CROSS-REFERENCE TO RELATED APPLICATION

This application is based on and claims priority under 35 U.S.C. § 119 to Korean Patent Application No. 10-2020-0072335, filed on Jun. 15, 2020, in the Korean Intellectual Property Office, the disclosure of which is incorporated by reference herein in its entirety.

BACKGROUND

1. Field

The disclosure relates to a wearable device, such as smart earphones, a smart ring, smart glasses, a smart necklace, smart earrings, and the like, and a method of measuring bio-signals using the same.

2. Description of Related Art

Photoplethysmography (PPG) is a general non-invasive technique for measuring bio-signals. In the technique, bio-signals are measured by emitting light to a body surface using a light source, and an amount of light reflected from tissues or blood vessels in the skin is measured using a light receiving sensor. In this case, a heart rate may be measured by measuring a relative change of blood flow in blood vessels based on a change in amplitude of continuously measured light signals, and a cardiovascular index, such as blood pressure, blood glucose, triglycerides, and the like, may be analyzed by analyzing a shape of signals. In order to measure photoplethysmography signals, a light source and a light receiving element are required, in which the light source consumes most of power during measurement of photoplethysmography signals. Since smart wearable systems are intended to be worn and used conveniently by users during daily activities, the smart wearable systems are manufactured to be lightweight in a compact size, thereby limiting a mountable battery capacity. Accordingly, there is a need to optimize power consumption in order to properly commercialize measurement of bio-signals based on photoplethysmography in the smart wearable systems.

SUMMARY

In accordance with an aspect of the disclosure, a wearable device includes an external light collector configured to collect external light; a sensor including an auxiliary light source and a light receiver, the sensor being configured to measure a bio-signal of an object; and a processor configured to determine whether the external light is sufficient to measure the bio-signal, and to control driving of the auxiliary light source based on the determination.

The sensor may measure the bio-signal using only the external light when the auxiliary light source is turned off at an early stage of measurement of the bio-signal.

The processor may be configured to extract a low-frequency band signal component of the bio-signal measured using only the external light when the auxiliary light source is turned off at the early stage of measurement of the bio-signal, and to determine whether the external light is sufficient to measure the bio-signal based on an amplitude of the extracted low-frequency band signal component.

In response to a first determination that the external light is sufficient to measure the bio-signal, the processor may be configured to maintain the auxiliary light source in an off state, and in response to a second determination that the external light is insufficient to measure the bio-signal, the processor may be configured to turn on the auxiliary light source.

The wearable device may further include a battery configured to supply power to the auxiliary light source, wherein in response to the second determination that the external light is insufficient to measure the bio-signal, the processor is configured to check a state of charge of the battery, and determine whether to turn on the auxiliary light source based on the checked state of charge.

The wearable device may include at least one from among smart earphones, a smart ring, a smart necklace, smart earrings, a smart watch, and smart glasses.

The wearable device may further include a main body worn on the object, wherein the external light collector is integrally formed in an area of the main body which is exposed to an outside of the object when the main body is worn on the object.

The wearable device may further include a main body worn on the object, wherein the external light collector is detachably provided in an area of the main body which is exposed to an outside of the object when the main body is worn on the object.

The external light collector may include a lens, and the lens may include an optical filter or may be formed of a predetermined color so as to pass a predetermined wavelength of the external light.

The external light collector may include a waveguide configured to transmit the collected external light to the object.

The light receiver may include a complementary metal-oxide semiconductor (CMOS) image sensor.

The wearable device may include a communication interface configured to transmit the bio-signal, measured by the sensor, to an external device.

The wearable device may include a storage configured to store the bio-signal measured by the sensor.

In accordance with an aspect of the disclosure, a method of measuring a bio-signal includes collecting external light using an external light collector; measuring the bio-signal of an object using a light receiver; determining using a processor whether the external light is sufficient to measure the bio-signal; and controlling, by the processor, of driving of an auxiliary light source based on the determination.

The measuring of the bio-signal may include measuring the bio-signal using only the external light when the auxiliary light source is turned off at an early stage of measurement of the bio-signal.

The determining whether the external light is sufficient to measure the bio-signal may include extracting a low-frequency band signal component of the bio-signal measured using only the external light, and determining whether the external light is sufficient to measure the bio-signal based on an amplitude of the extracted low-frequency band signal component.

The controlling of the driving of the auxiliary light source may include, in response to a first determination that the external light is sufficient to measure the bio-signal, maintaining the auxiliary light source in an off state, and in response to a second determination that the external light is insufficient to measure the bio-signal, turning on the auxiliary light source.

The method may further include transmitting the measured bio-signal to an external device.

The method may further include storing the measured bio-signal.

In accordance with an aspect of the disclosure, an apparatus for estimating bio-information includes a first device including an external light collector configured to collect external light, the first device being configured to measure a bio-signal of an object; determine whether the external light is sufficient to measure the bio-signal; control driving of an auxiliary light source based on the determination; and transmit the measured bio-signal to a second device; and a second configured to receive the bio-signal from the first device and estimate the bio-information based on the received bio-signal.

The first device may be configured to measure the bio-signal using only the external light when the auxiliary light source is turned off at an early stage of measurement of the bio-signal.

The first device may be configured to extract a low-frequency band signal component of the bio-signal measured using only the external light when the auxiliary light source is turned off at the early stage of measurement of the bio-signal, and determine whether the external light is sufficient to measure the bio-signal based on an amplitude of the extracted low-frequency band signal component.

In response to a first determination that the external light is sufficient to measure the bio-signal, the first device may be configured to maintain the auxiliary light source in an off state, and in response to a second determination that the external light is insufficient to measure the bio-signal, the first device may be configured to turn on the auxiliary light source.

The second device may be configured to receive information on a state of charge of a battery of the first device, and control measuring of the bio-signal or charging of the battery based on the received information.

The bio-information may include one or more from among a blood pressure, a vascular age, an arterial stiffness, an aortic pressure waveform, a vascular compliance, a stress index, and a fatigue level.

In accordance with an aspect of the disclosure, a device includes a sensor configured to measure a bio-signal of a user of the device; a light source; and a processor configured to operate the light source based on the measured bio-signal.

The processor may be configured to extract a component of a first bio-signal measured when the light source is off; and operate the light source based on the extracted component.

The processor may be configured to determine an amplitude of the extracted component; and operate the light source based on the determined amplitude.

The processor may be configured to operate the light source based on a difference between the determined amplitude and a threshold amplitude.

The processor may be configured to, in response to the determined amplitude being greater than or equal to a threshold amplitude, control the sensor to measure a second bio-signal when the light source is off; and in response to the determined amplitude being less than the threshold amplitude, turn on the light source and control the sensor to measure the second bio-signal when the light source is on.

DETAILED DESCRIPTION

Figure 1:
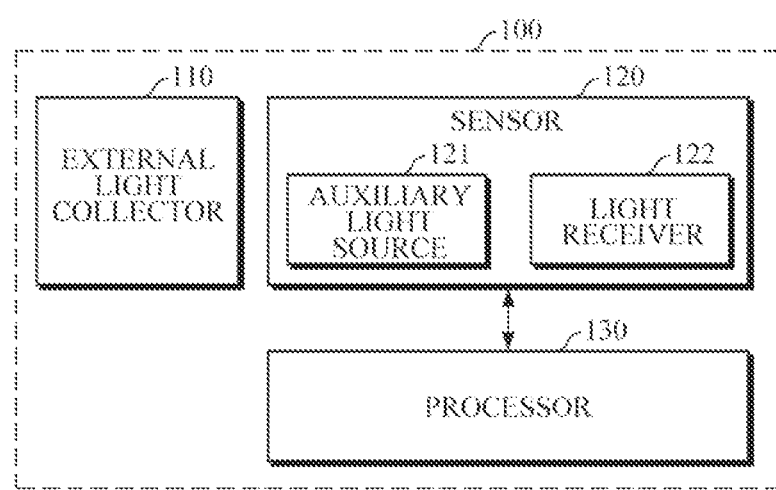
FIG. 1 is a block diagram illustrating a wearable device according to an embodiment.

Details of o embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" or "including" another element, the element is intended not to exclude one or more other elements, but to further include one or more other elements, unless explicitly described to the contrary. In the following description, terms such as "unit" and "module" indicate a unit for processing at least one function or operation that may be implemented by using hardware, software, or a combination thereof.

Hereinafter, embodiments of a wearable device and a method of measuring a bio-signal using the same will be described in detail with reference to the accompanying drawings. Various embodiments of the wearable device may include, but are not particularly limited to, smart earphones, a smart ring, smart glasses, a smart necklace, smart earrings, a smart watch, a Head Mounted Display (HMD), and the like.

FIG. 1 is a block diagram illustrating a wearable device according to an embodiment.

Referring to FIG. 1, the wearable device 100 includes an external light collector 110, a sensor 120, and a processor 130. The external light collector 110 may be disposed in a main body area, which is exposed to the outside of the main body when the main body of the wearable device 100 is worn on an object. In this case, the object may be a body part of a user, which comes into contact with the main body of the wearable device 100, and may be various parts including an inner or outer portion of the ear, a finger, a neck, a nose, and the like. The external light collector 110 may have various shapes according to a shape of the main body.

For example, the external light collector 110 may include a lens for collecting light. If the wearable device 100 includes earphones, a ring, and the like, the lens may be a convex lens which may be disposed on a surface of the wearable device 100. However, the external light collector 110 is not limited thereto, and may be modified to various shapes, such as a cylindrical shape, a polygonal shape, and the like, to be harmonized with various shapes of the wearable device 100.

In addition, the external light collector 110 may include a waveguide to transmit the collected external light to an object which comes into contact with the main body when the main body is worn by the user. The waveguide may include an optical fiber. However, the external light collector 110 is not limited thereto, and a travel path of the external light to the object may be modified variously according to a distance between the lens of the external light collector 110 and the object, a structure of the main body, and the like. For example, a light path may be formed in a hollow space between the lens and a contact region of the object. In this case, the external light collector 110 may include an optical filter for passing light in a specific wavelength band which is then collected by the lens. Alternatively, the lens may be formed of a specific color for passing a specific wavelength of the external light.

The sensor 120 may include an auxiliary light source 121 and a light receiver 122. The sensor 120 may transmit external light and/or may emit light of the auxiliary light source 121 onto the object, and may acquire a bio-signal using the light receiver 122 by detecting light scattered or reflected from the object. In this case, the bio-signal may include a photoplethysmography (PPG) signal, but is not limited thereto.

The auxiliary light source 121 may emit auxiliary light onto the object, and may include a light emitting diode (LED), a laser diode, a tungsten halogen lamp, and the like. The auxiliary light source 121 may be formed as one light source or an array of a plurality of light sources. In this case, the plurality of auxiliary light sources 121 may emit light of different wavelengths. Further, at least some of the plurality of auxiliary light sources 121 may have different power consumption levels.

The light receiver 122 may detect scattered or reflected light when light collected and transmitted by the external light collector 110 and/or light emitted by the auxiliary light source 121 are scattered or reflected from the surface of the object or internal body tissues beneath the surface of the object. The light receiver 122 may include a complementary metal-oxide semiconductor (CMOS) image sensor, but is not limited thereto, and may include a photodiode, a photo transistor, a charge-coupled device (CCD) image sensor, and the like.

In addition, the sensor 120 may include an external light transmitter, which is connected to the waveguide of the external light collector 110 to transmit the external light to the object. The external light transmitter may be disposed between the auxiliary light source 121 and the light receiver 122, but its position is not limited thereto. Further, the external light transmitter may be separated from the auxiliary light source 121 and the light receiver 122 by a partition wall.

The processor 130 may be electrically connected to the sensor 120. The processor 130 may control the sensor 120 to measure bio-signals. Once the main body is worn on the object, the processor 130 may control the sensor 120 to measure bio-signals continuously at predetermined time intervals.

In order to minimize power consumption when the sensor 120 measures bio-signals, the processor 130 may control the sensor 120 to measure bio-signals using only the external light without turning on the auxiliary light source 121. Furthermore, when the sensor 120 measures bio-signals using only the external light, the processor 130 may determine whether the external light is sufficient to measure the bio-signals; and if the external light is not sufficient, the processor 130 may adjust an amount of light emitted to the object by turning on the auxiliary light source 121.

While the sensor 120 measures bio-signals using only the external light, the processor 130 may extract a low-frequency band signal component by performing low-pass filtering on the bio-signals, and may determine whether the external light is sufficient based on an amplitude of the extracted low-frequency band signal component. For example, if an amplitude of the extracted low-frequency band signal component is less than a predetermined threshold value, the processor 130 may determine that the external light is not sufficient, and may turn on the auxiliary light source 121. If an amplitude of the extracted low-frequency band signal component is greater than or equal to the predetermined threshold value, the processor 130 may determine that the external light is sufficient, and may maintain the auxiliary light source 121 in an off state.

Furthermore, based on a difference between the amplitude of the low-frequency band signal component, which is measured using the external light, and the predetermined threshold value, the processor may adjust an amount of light emitted by the auxiliary light source 121 in stages. For example, the processor 130 may divide differences between the low-frequency band signal component and the predetermined threshold value into multiple stages (e.g., three stages), and may control the auxiliary light source 121 to emit a different amount of light for each stage. Alternatively, in the case where a plurality of auxiliary light sources 121 are present and have different power consumption levels, the processor 130 may consider each power consumption level of the auxiliary light sources 121 and may drive the appropriate auxiliary light source 121 which is suitable for a stage corresponding to the difference between the low-frequency band signal component and the predetermined threshold value. In this case, driving conditions of the auxiliary light source 121 may be pre-defined.

As described above, by controlling driving of the auxiliary light source 121 in real time based on whether the external light is sufficient, the processor 130 may control the sensor 120 to effectively measure bio-signals from the object while minimizing power consumption.

Figure 2:
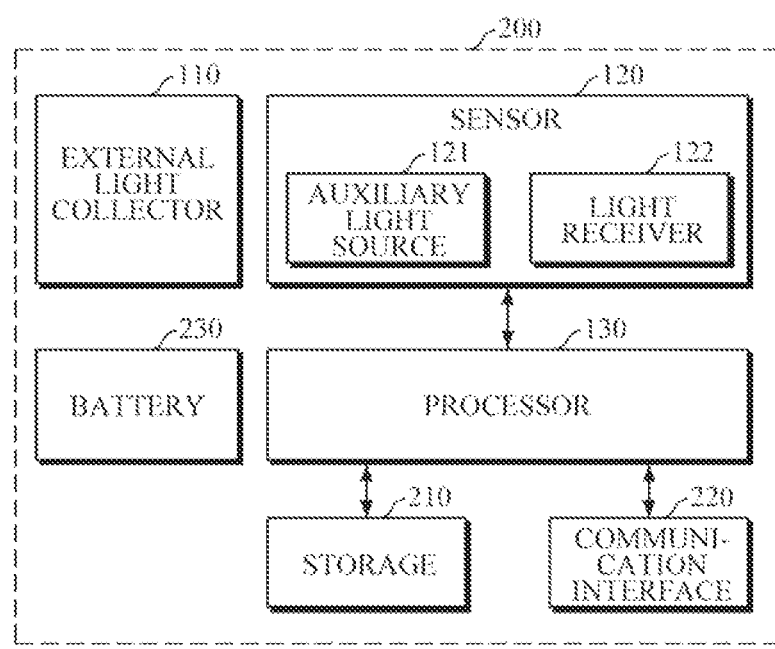
FIG. 2 is a block diagram illustrating a wearable device according to an embodiment.

FIG. 2 is a block diagram illustrating a wearable device according to an embodiment.

Referring to FIG. 2, the wearable device 200 includes the external light collector 110, the sensor 120, the processor 130, a storage 210, a communication interface 220, and a battery 230. The external light collector 110, the sensor 120, and the processor 130 are described above in detail, such that redundant description thereof will be omitted.

The storage 210 may store a variety of information related to measuring bio-signals. For example, the storage 210 may store a bio-signal measuring cycle, driving conditions of the auxiliary light source 121, e.g., a low-frequency band signal component of the bio-signal measured using the external light, a threshold value used as criteria for comparison, stages of differences between the low-frequency band signal component and the threshold value, information of the auxiliary light source 121 to be driven for each stage, and the like. In addition, the storage 210 may store condition information on whether to measure bio-signals according to a battery status, whether to drive the auxiliary light source 121, and the like. Further, the storage 210 may store user characteristic information such as a user's age, sex, stature, weight, health condition, and the like. However, the stored information is not limited thereto.

In this case, the storage 210 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 220 may communicate with an external device by using wired or wireless communication techniques under the control of the processor 130, and may transmit and receive various data to and from the external device. For example, the communication interface 220 may receive from the external device a request for measuring a bio-signal or a request for providing a measured bio-signal, and may transmit the measured bio-signal to the external device. In addition, the communication interface 220 may transmit status information of the battery 230, e.g., information on a residual capacity of the battery 230, to the external device. In this case, the external device may include a cuff-type blood pressure measuring device, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are merely examples and are not intended to be limiting.

The battery 230 may provide power to the sensor 120, the processor 130, the storage 210, the communication interface 220, and various other modules of the wearable device 200. The battery 230 may be integrally formed with the wearable device 200 or may be detachably mounted therein. The battery 230 may receive power from an external source by wire or wirelessly.

The processor 130 may check a state of the battery 230, e.g., a residual battery capacity, and may control the sensor 120 based on the residual battery capacity. For example, if it is determined that external light is not sufficient for the sensor 120 to measure a bio-signal, and thus it is required to drive the auxiliary light source 121, the processor 130 checks a residual battery capacity. If the residual battery capacity is less than or equal to a predetermined threshold (e.g., 20%), the processor 130 may control the sensor 120 to continuously measure the bio-signal without driving the auxiliary light source 121, or may control the sensor 120 to stop measuring the bio-signal.

Alternatively, the processor 130 may subdivide the residual battery capacity into stages and may control the sensor 120 under different conditions for each stage. For example, the processor 130 may divide the residual battery capacity into a first stage (20% to 10%), a second stage (10% to 5%), and a third stage (5% or less). If the residual battery capacity is in the first stage, the processor 130 may drive the auxiliary light source 121 having a low power consumption; in the second stage, the processor 130 may control the sensor 120 to continuously measure the bio-signal without driving the auxiliary light source 121; and in the third stage, the processor 130 may control the sensor 120 to stop measuring the bio-signal. In this case, control conditions of the sensor 120 according to the residual battery capacity may be pre-defined and stored in the storage 210.

FIGS. 3A to 5D are diagrams illustrating various examples of wearable devices. The wearable devices illustrated in FIGS. 3A to 5D are merely examples. Accordingly, embodiments are not limited to the illustrated wearable devices, but may be applied to various other types of wearable devices. The following description will be focused on the external light collector 110 and the sensor 120 with reference to FIGS. 3A to 5D. The processor 130, the battery 230, and the like are disposed in a main body MB and may be electrically connected to the sensor 120, but the configuration thereof is omitted from FIGS. 3A to 5D to reduce complexity thereof.

Figure 3A:
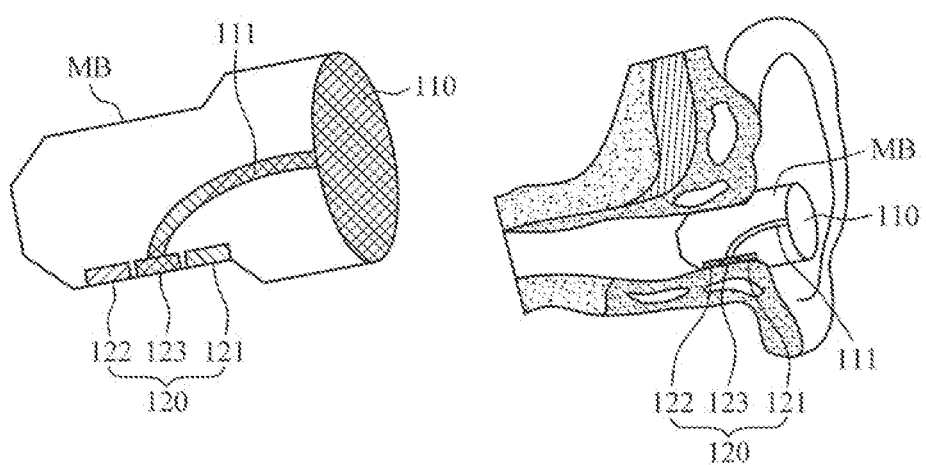
FIGS. 3A, 3B, 4A, 4B, and 5A to 5D are diagrams illustrating various examples of wearable devices.
Figure 3B:
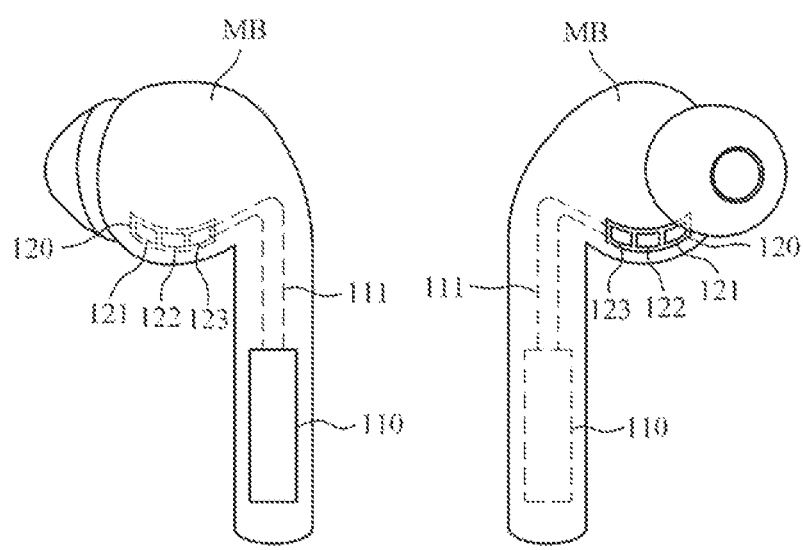

Referring to FIGS. 3A and 3B, the wearable device 100 may be smart earphones. The smart earphones may be Bluetooth earphones, wired earphones, neckband type earphones, bone-conduction earphones, and the like, and are not limited to any one of these earphones.

As illustrated in FIGS. 3A and 3B, in the case where an earphone main body MB is inserted into the ear, the sensor 120 may be disposed in an area which is in contact with an inner portion of the ear. The sensor 120 may include the auxiliary light source 121, the light receiver 122, and the external light transmitter 123 as illustrated herein. The auxiliary light source 121, the light receiver 122, and the external light transmitter 123 of the sensor 120 may be disposed one by one in a specific area (e.g., lower end as shown in FIGS. 3A and 3B) of the main body MB which is in contact with the ear. However, the arrangement is not limited thereto, and a plurality of auxiliary light sources 121, light receivers 122, and external light transmitters 123 may be disposed in circular, oval, rectangular, and triangular shapes along a portion of the main body area being in contact with the ear, or on an upper end and a lower end of the main body with no limitation to their shapes.

Further, as illustrated herein, the external light collector 110 may be disposed in an area of the main body MB which is exposed to an outside of the ear when the main body MB is in contact with the ear. The external light collector 110 may include a lens, and the waveguide 111 so that external light, collected by the lens, may be transmitted to the external light transmitter 123 to be transmitted to the inner portion of the ear.

As illustrated in FIGS. 3A and 3B, the external light collector 110 may be disposed at various positions, at which the external light may be collected effectively, according to a shape of the main body MB. The external light collector 110 may be disposed at an appropriate position to be harmonized with a shape of the main body MB. Further, the lens of the external light collector 110 may be formed in various shapes, e.g., circle, polygon, oval, etc., to provide aesthetic effects for a user, or may be formed with a particular design having aesthetic characteristics, such as flower patterns and the like. The lens of the external light collector 110 may be formed in a particular color to pass a specific wavelength of the external light and/or to have aesthetic characteristics.

If smart earphones are neckband type earphones, the sensor 120 may be disposed on an inner surface of a neckband portion, so that the sensor 120 may come into contact with the skin of the neck. The external light collector 110 may be disposed at a position where the external light may be collected easily, such as an outer surface of the neckband portion or an outer surface of a portion to which an ear cap is attached. Further, if smart earphones are earring type earphones, the sensor 120 may be disposed on an inner surface of a ring portion of the earring earphone main body. The external light collector 110 may be disposed on an outer surface of the ring portion of the main body.

Figure 4A:
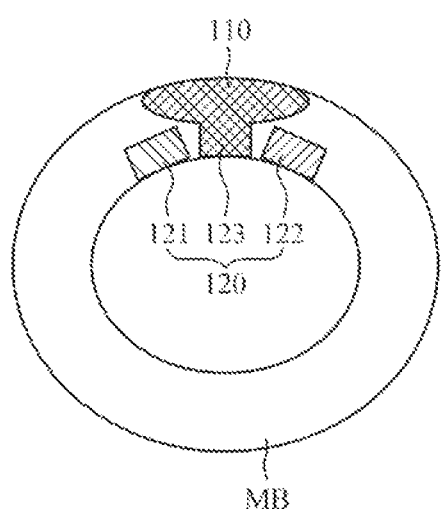
Figure 4B:
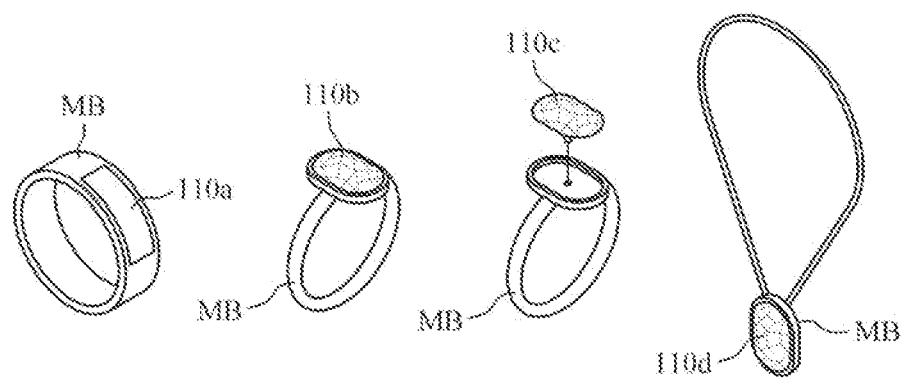

Referring to FIGS. 4A and 4B, the wearable device 100 may be a smart ring or a smart necklace.

As illustrated in FIGS. 4A and 4B, when a main body MB of the smart ring is worn on a finger, the auxiliary light source 121, the light receiver 122, and the external light transmitter 123 of the sensor 120 may be disposed on an inner portion of the main body MB which is in contact with the finger, and the external light collector 110 may be disposed on an outer portion of the main body MB. As illustrated herein, the sensor 120 may be disposed in an area of the main body MB being in contact with one side of the finger (back of the finger), but is not limited thereto, and may be disposed in a circular shape on an inner portion of the main body MB or may be disposed in upper/lower/left/right areas thereof. Depending on a thickness of the main body MB, the external light transmitter 123 may have a hole formed in the light path, and may be directly connected to the external light collector 110 to transmit the external light onto the finger.

As illustrated in FIG. 4B, the external light collector 110 may have a convex lens shape 110a or may have various gem shapes 110b and 110c according to the shape of the main body MB. In this case, the external light collector 110 may have a shape 110b which is integrally formed with the main body MB, or may have a shape 110c which is detachably connected to the main body MB.

As illustrated in FIG. 4B, the wearable device 100 may be a smart necklace type wearable device, in which the sensor 120 is disposed on a back surface of a pendant MB of the necklace, which is in contact with the skin, and the external light collector 110d may be disposed on a front surface of the pendant MB.

Referring to FIGS. 5A to 5D, the wearable device 100 may be smart glasses.

Figure 5A:
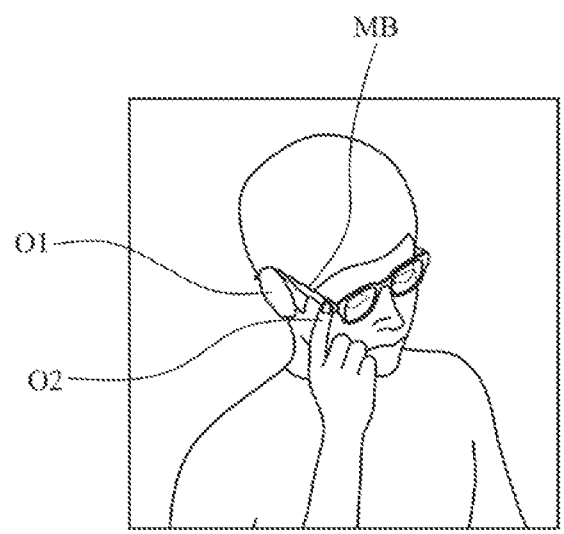

Referring to FIG. 5A, the sensor 120 may be disposed in an area of the main body MB which comes into contact with various body parts, so that the sensor 120 may measure bio-signals from various body parts, such as a nose bridge, a portion near the ear O1, the finger O2, and the like while a user wears the glasses.

Figure 5B:
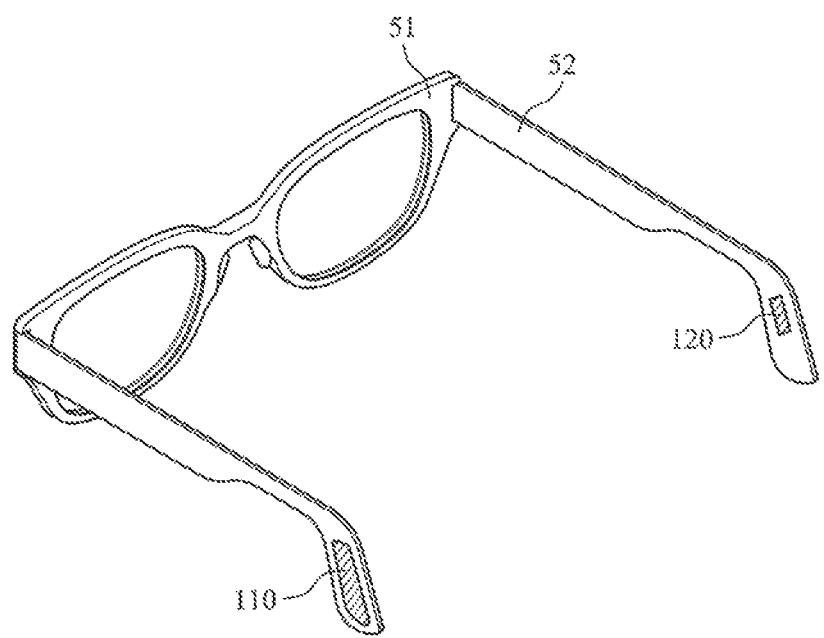

Referring to FIG. 5B, the sensor 120 may be disposed on an inner portion of temple tips of spectacle temples (i.e., earpieces) 52, so as to measure a bio-signal near the ear, on which the spectacle temples 52 rest when the glasses are worn. In this case, the external light collector 110 may be disposed on an outer portion of the temple tips of the spectacle temples 52. FIG. 5B illustrates an example in which the external light collector 110 and the sensor 120 are disposed on each of the left and right spectacle temples 52. However, this is merely intended to assist in understanding, and the external light collector 110 and the sensor 120 may be disposed on only the left or only the right spectacle temple 52 or on both spectacle temples 52.

Figure 5C:
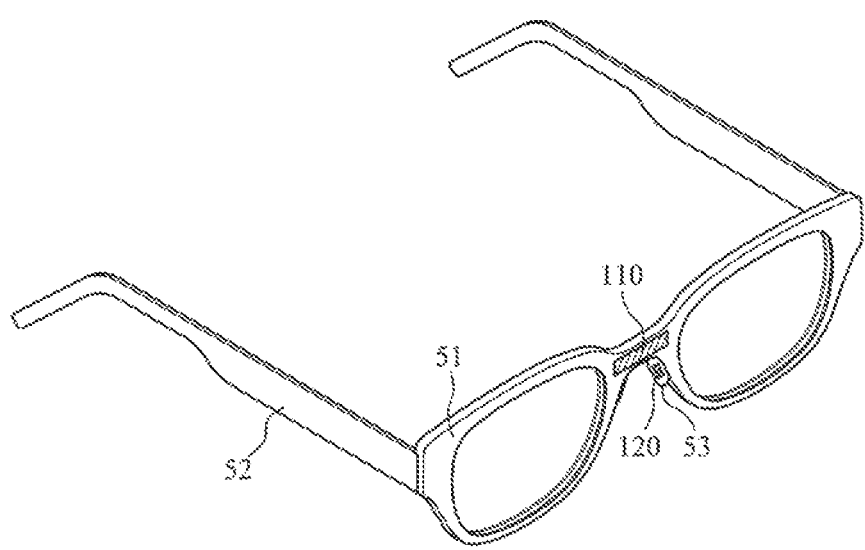

Referring to FIG. 5C, the sensor 120 may be disposed on an inner portion of a nose pad 53, so as to measure a bio-signal near the nose, on which the nose pad 53 rests when the glasses are worn. In this case, the external light collector 110 may be disposed on an outer portion of a front frame 51 of the main body. The external light collector 110 and the sensor 120 may be connected via a waveguide.

Figure 5D:
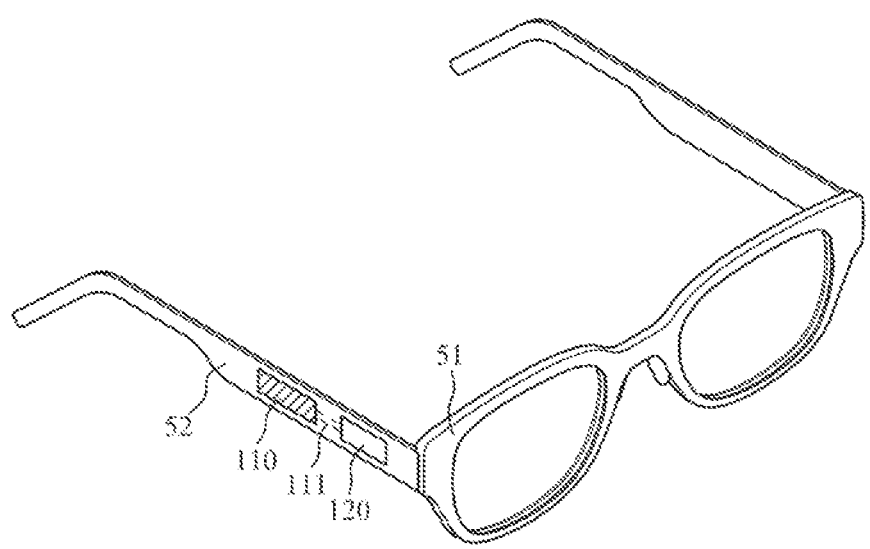

Referring to FIG. 5D, the sensor 120 may be disposed on an outer surface of the spectacle temples 52 so that the sensor 120 may measure a bio-signal from a finger when the glasses are worn, and the external light collector 110 may be disposed next to the sensor 120. As illustrated in FIG. 5A, when a user touches the sensor 120 with a finger while wearing the glasses, the sensor 120 may measure a bio-signal from the finger. The sensor 120 and the external light collector 110 may be disposed on either or both spectacle temples 52.

Figure 6A:
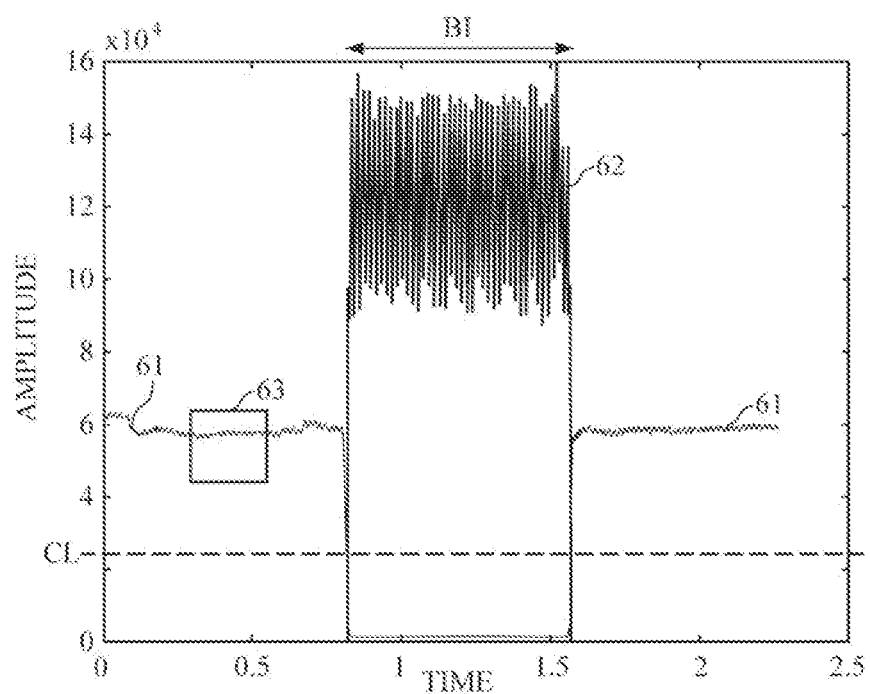
FIGS. 6A to 6C are diagrams explaining an example of measuring a pulse wave signal according to an embodiment.
Figure 6B:
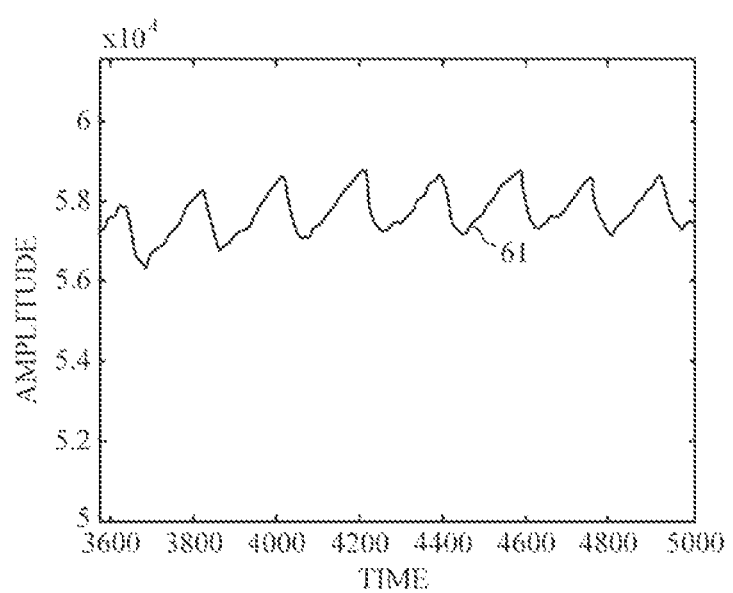
Figure 6C:
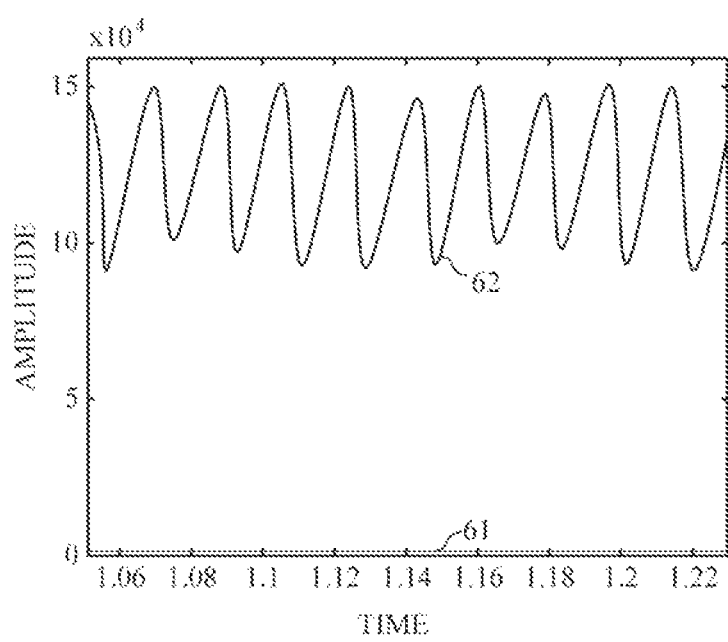

FIGS. 6A to 6C are diagrams explaining an example of measuring a pulse wave signal according to an embodiment.

FIG. 6A is a diagram illustrating a bio-signal measured by the sensor 120 for a predetermined period of time. FIG. 6B is a diagram illustrating a bio-signal 61 in an interval 63, in which an amplitude of a low-frequency band signal component, measured using only external light, is greater than or equal to a predetermined threshold value. FIG. 6C is a diagram illustrating a bio-signal 62 measured when driving an auxiliary light source in an interval BI, in which the external light is blocked.

As illustrated in FIGS. 6A to 6C, when measurement is started at time 0, the processor 130 may maintain the auxiliary light source 121 in an off state so that a pulse wave signal may be measured using only the external light. While the sensor 120 measures the pulse wave signal 61 by using only the external light, the processor 130 may extract a low-frequency band signal component of the pulse wave signal 61, and may determine whether an amplitude of the low-frequency band signal component is greater than or equal to a predetermined threshold value CL. If an amplitude of the low-frequency band signal component is determined to be greater than or equal to the predetermined threshold value CL, the processor 130 may determine that the external light is sufficient to measure the pulse wave signal, and may continuously maintain the auxiliary light source 121 in an off state. Further, if the external light is blocked or is insufficient in the predetermined interval BI while the pulse wave signal is measured, such that an amplitude of the low-frequency band signal component decreases to less than the threshold value CL, the processor 130 may turn on the auxiliary light source 121, such that the pulse wave signal 62 may be measured under the auxiliary light source 121. In addition, if the external light is determined to be sufficient again after the predetermined interval BI, the processor 130 may then turn off the auxiliary light source 121.

According to the embodiments disclosed above, while wearing various types of wearable devices 100 when staying in a bright place or a dark place or moving between bright and dark areas, or regardless of whether it is day or night or regardless of time and place, a user may measure bio-signals conveniently with low battery consumption.

Figure 7:
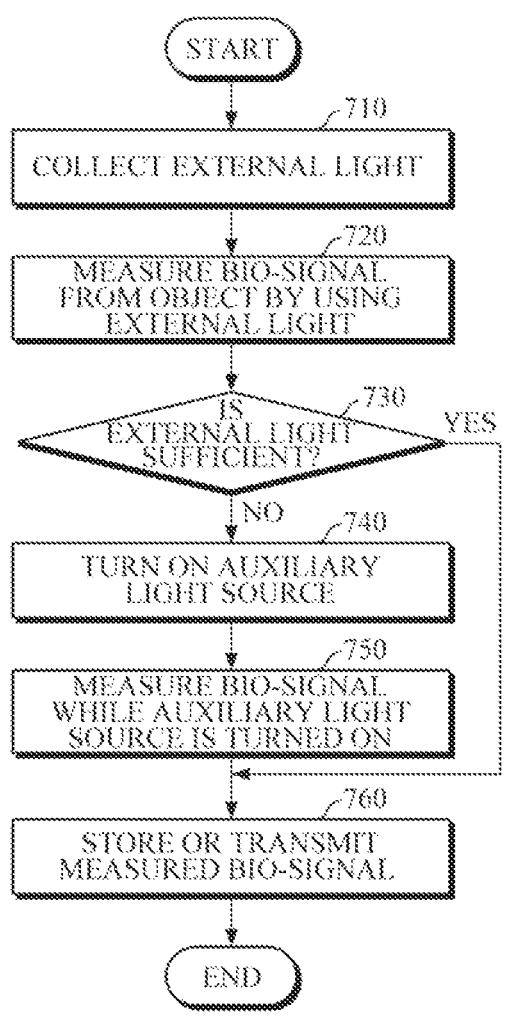
FIG. 7 is a diagram illustrating a method of measuring a bio-signal according to an embodiment.

FIG. 7 is a diagram illustrating a method of measuring a bio-signal according to an embodiment.

FIG. 7 is a diagram illustrating a method of measuring a bio-signal, which is performed by the wearable devices 100 and 200 according to the embodiments of FIGS. 1 and 2, which are described above in detail, and thus will be briefly described below.

The wearable devices 100 and 200 may collect external light by using an external light collector disposed at a main body in 710. The external light collector is disposed in an area which is exposed to the outside of an object such as a user when the main body is worn, such that the external light collector may collect the external light at normal times when the main body of the wearable devices 100 and 200 is worn by the user.

Then, in response to a request for measuring a bio-signal, the wearable devices 100 and 200 may measure a bio-signal by a sensor using the external light in 720. The sensor is disposed in a main body area which is in contact with the object, such that the sensor may transmit the light, collected by the external light collector, onto the object. In this case, the external light collector includes a waveguide, through which the external light collector may be connected to the sensor.

Subsequently, the wearable devices 100 and 200 may determine whether the external light is sufficient to measure the bio-signal based on the bio-signal measured using the external light in 730. For example, the wearable devices 100 and 200 may extract a low-frequency band signal component by performing low-pass filtering on the bio-signal measured using the external light, and if an amplitude of the extracted low-frequency band signal component is greater than or equal to a predetermined threshold value, the wearable devices 100 and 200 may determine that the external light is sufficient. As described above, upon determining that the external light is sufficient, the processor may proceed to operation 760.

If an amplitude of the extracted low-frequency band signal component is less than the predetermined threshold value, the wearable devices 100 and 200 may determine that the external light is not sufficient, and may turn on the auxiliary light source in 740.

Next, the wearable devices 100 and 200 may continuously measure the bio-signal while the auxiliary light source is turned on in 750.

Then, the wearable devices 100 and 200 may store the measured bio-signal or may transmit the measured bio-signal to an external device in 760.

Figure 8:
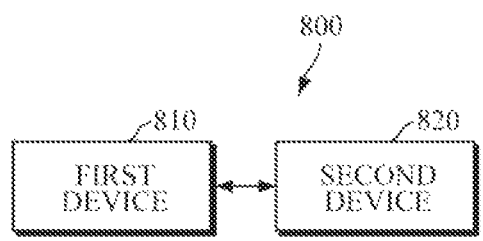
FIG. 8 is a block diagram illustrating an apparatus for estimating bio-information according to an embodiment.
Figure 9:
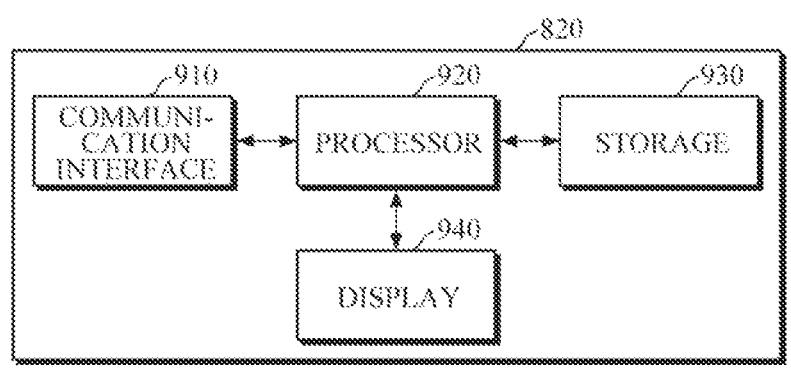
FIG. 9 is a block diagram illustrating a second device of the apparatus for estimating bio-information according to an embodiment.

FIG. 8 is a block diagram illustrating an apparatus for estimating bio-information according to an embodiment. FIG. 9 is a block diagram illustrating a second device of the apparatus for estimating bio-information according to an embodiment.

Referring to FIG. 8, the apparatus 800 for estimating bio-information includes a first device 810 and a second device 820. FIG. 9 illustrates the second device 820.

The first device 810 may be the aforementioned wearable devices 100 and 200. The first device 810 may include an external light collector, a sensor, a processor, a storage, a communication interface, and the like as described above, and detailed description thereof will be omitted.

The second device 820 may be a mobile device, such as a smartphone, a tablet PC, and the like which is carried by a user, but is not limited thereto, and may include a desktop computer, a laptop computer, servers of medical institutions, and the like.

The second device 820 includes a communication interface 910, a processor 920, a storage 930, and a display 940.

The communication interface 910 of the second device 820 may communicate with the communication interface of the first device 810 by wire or wirelessly according to a connection method, and may transmit a request for measuring a bio-signal to the first device 810 and receive a measured bio-signal from the first device 810.

The processor 920 may receive a user's request for measuring bio-information, and may transmit a request for measuring a bio-signal to the first device 810 through the communication interface 910.

While the first device 810 measures a bio-signal, the processor 920 may receive from the communication interface 910 information on a state of the battery of the first device 810, e.g., information on a residual battery capacity. Upon receiving the information on the state of the battery of the first device 810, the processor 920 may control charging of the battery or measuring of the bio-signal of the first device 810 through wired or wireless communication. For example, upon determining that a residual battery capacity of the first device 810 is not sufficient to measure the bio-signal, the processor 920 may control the battery of the first device 810 to be charged using the battery of the second device 820 by wire/wirelessly according to a battery charging method. Alternatively, if a residual battery capacity of the second device 820 is not sufficient to charge the battery of the first device 810, the processor 920 may transmit a request for stopping measurement of the bio-signal.

Upon receiving the measured bio-signal from the first device 810, the processor 920 may remove noise from the bio-signal by various preprocessing operations, including a band-pass filtering. Further, the processor 920 may obtain features for estimating bio-information from the bio-signal, and may estimate bio-information by using the obtained features. In this case, the bio-information may include one or more of blood pressure, vascular age, arterial stiffness, aortic pressure waveform, vascular compliance, stress index, and fatigue level, but is not limited thereto.

For example the processor 920 may obtain, as features, a maximum point and a minimum point of the bio-signal, a heart rate, amplitude and time values at points related to propagation and reflection pulse waves, an area of a predetermined interval of a waveform of the bio-signal, and the like, and may estimate bio-information by using a combination of the obtained one or more features and a pre-defined bio-information estimation model. Alternatively, the processor 920 may estimate bio-information using oscillometry based on contact pressure between an object and the sensor of the first device 810 while the bio-signal is measured.

The storage 930 may store the bio-signal received from the first device 810. The first device 810 may measure bio-signals continuously at predetermined intervals while the first device 810 is worn on a user, and upon completing measurement of the bio-signals, the first device 810 may transmit the measured bio-signals to the second device 820 so that the second device 820 may manage a bio-signal measurement history. In this case, in addition to measuring the bio-signal by controlling the first device 810 in response to a user's request for measuring a bio-signal, the processor 920 may estimate bio-information by using a latest periodic bio-signal that has been stored in the storage 930 after being received from the first device 810.

Further, the storage 930 may store results processed by the processor 920, e.g., estimated bio-information values. In addition, the storage 930 may store a bio-information estimation model, reference information such as a user's condition information, and the like.

The display 940 may display and provide processing results of the processor 920 for a user. The display 940 may include a touch screen for receiving a user's input, and may transmit a user's touch input to the processor 920. While the first device 810 measures a bio-signal, the display 940 may display a state of charge of the battery of the first device 810, an on/off state of the auxiliary light source, progress of measurement of the bio-signal, the measured bio-signal itself, the estimated bio-information value, analysis information on a user's health condition according to a bio-information estimation result, and the like. Further, the second device 820 may provide a user with information, related to the estimated bio-information, in a non-visual manner by voice, vibrations, tactile sensation, and the like using output modules such as a speaker, a haptic module, and the like which are embedded therein or included in a connected external device.

The disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the disclosure can be readily deduced by programmers in the technical field to which the disclosure pertains.

The disclosure has been described herein with regard to preferred embodiments. However, it will be obvious to those skilled in the art that various changes and modifications can be made without changing technical conception and essential features of the disclosure. Thus, it is clear that the above-described embodiments are illustrative in all aspects and are not intended to limit the disclosure.

What is claimed is:

1. A wearable device, comprising:
   an external light collector configured to collect external light;
   a sensor comprising an auxiliary light source and a light receiver, the sensor being configured to measure a bio-signal of a user; and
   a processor configured to determine whether the external light is sufficient to measure the bio-signal, and to control driving of the auxiliary light source based on the determination,
   wherein the processor is configured to extract a frequency component by filtering the bio-signal measured using only the external light when the auxiliary light source is turned off at an early stage of measurement of the bio-signal, and to determine whether the external light is sufficient to measure the bio-signal based on an amplitude of the extracted frequency component.

2. The wearable device of claim 1, wherein in response to a first determination that the external light is sufficient to measure the bio-signal, the processor is configured to maintain the auxiliary light source in an off state, and in response to a second determination that the external light is insufficient to measure the bio-signal, the processor is configured to turn on the auxiliary light source.

3. The wearable device of claim 2, further comprising a battery configured to supply power to the auxiliary light source,
   wherein in response to the second determination that the external light is insufficient to measure the bio-signal, the processor is configured to check a state of charge of the battery, and determine whether to turn on the auxiliary light source based on the checked state of charge.

4. The wearable device of claim 1, wherein the wearable device comprises at least one from among smart earphones, a smart ring, a smart necklace, smart earrings, a smart watch, and smart glasses.

5. The wearable device of claim 1, further comprising a main body worn on the user,
   wherein the external light collector is integrally formed in an area of the main body which is exposed to an outside of the user when the main body is worn on the user.

6. The wearable device of claim 1, further comprising a main body worn on the user,
   wherein the external light collector is detachably provided in an area of the main body which is exposed to an outside of the user when the main body is worn on the user.

7. The wearable device of claim 1, wherein the external light collector comprises a lens, and
   wherein the lens comprises an optical filter or is formed of a predetermined color so as to pass a predetermined wavelength of the external light.

8. The wearable device of claim 1, wherein the external light collector comprises a waveguide configured to transmit the collected external light to the user.

9. The wearable device of claim 1, wherein the light receiver comprises a complementary metal-oxide semiconductor (CMOS) image sensor.

10. The wearable device of claim 1, further comprising a communication interface configured to transmit the bio-signal, measured by the sensor, to an external device.

11. The wearable device of claim 1, further comprising a storage configured to store the bio-signal measured by the sensor.

12. A method of measuring a bio-signal, the method comprising:
    collecting external light using an external light collector;
    measuring the bio-signal of a user using a light receiver;
    determining using a processor whether the external light is sufficient to measure the bio-signal; and
    controlling, by the processor, of driving of an auxiliary light source based on the determination,
    wherein the determining whether the external light is sufficient to measure the bio-signal comprises extracting a frequency component by filtering the bio-signal measured using only the external light, and determining whether the external light is sufficient to measure the bio-signal based on an amplitude of the extracted frequency component.

13. The method of claim 12, wherein the measuring of the bio-signal comprises measuring the bio-signal using only the external light when the auxiliary light source is turned off at an early stage of measurement of the bio-signal.

14. The method of claim 13, wherein the controlling of the driving of the auxiliary light source comprises, in response to a first determination that the external light is sufficient to measure the bio-signal, maintaining the auxiliary light source in an off state, and in response to a second determination that the external light is insufficient to measure the bio-signal, turning on the auxiliary light source.

15. The method of claim 13, further comprising transmitting the measured bio-signal to an external device.

16. The method of claim 13, further comprising storing the measured bio-signal.

17. An apparatus for estimating bio-information, the apparatus comprising:
    a first device comprising an external light collector configured to collect external light, the first device being configured to:
    measure a bio-signal of a user;
    determine whether the external light is sufficient to measure the bio-signal;
    control driving of an auxiliary light source based on the determination; and
    transmit the measured bio-signal to a second device; and
    the second device configured to receive the bio-signal from the first device and estimate the bio-information based on the received bio-signal, wherein the first device is configured to extract a frequency band signal component by filtering the bio-signal measured using only the external light when the auxiliary light source is turned off at an early stage of measurement of the bio-signal, and determine whether the external light is sufficient to measure the bio-signal based on an amplitude of the extracted frequency component.

18. The apparatus of claim 17, wherein in response to a first determination that the external light is sufficient to measure the bio-signal, the first device is configured to maintain the auxiliary light source in an off state, and in response to a second determination that the external light is insufficient to measure the bio-signal, the first device is configured to turn on the auxiliary light source.

19. The apparatus of claim 17, wherein the second device comprises a processor,
wherein the processor of the second device is configured to receive information on a state of charge of a battery of the first device, and control measuring of the bio-signal or charging of the battery based on the received information, and
wherein the processor of the second device is configured to control the charging of the battery of the first device using a battery of the second device.

20. The apparatus of claim 17, wherein the bio-information comprises one or more from among a blood pressure, a vascular age, an arterial stiffness, an aortic pressure waveform, a vascular compliance, a stress index, and a fatigue level.

21. A device comprising:
a sensor configured to measure a bio-signal of a user of the device;
a light source; and
a processor configured to operate the light source based on the measured bio-signal,
wherein the processor is configured to extract a frequency component by filtering the bio-signal measured using only external light when the light source is turned off at an early stage of measurement of the bio-signal, and to determine whether the external light is sufficient to measure the bio-signal based on an amplitude of the extracted frequency component.

22. The device of claim 21, wherein the processor is configured to determine the amplitude of the extracted frequency component; and operate the light source based on the determined amplitude.

23. The device of claim 22, wherein the processor is configured to operate the light source based on a difference between the determined amplitude and a threshold amplitude.

24. The device of claim 22, wherein the processor is configured to, in response to the determined amplitude being greater than or equal to a threshold amplitude, control the sensor to measure a second bio-signal when the light source is off; and in response to the determined amplitude being less than the threshold amplitude, turn on the light source and control the sensor to measure the second bio-signal when the light source is on.

* * * * *